(12) United States Patent
Hassan et al.

(10) Patent No.: US 10,722,736 B2
(45) Date of Patent: Jul. 28, 2020

(54) ROTATABLE CANTILEVER GANTRY IN RADIOTHERAPY SYSTEM

(71) Applicants: Varian Medical Systems, Inc., Palo Alto, CA (US); Varian Medical Systems Particle Therapy GmbH, Troisdorf (DE)

(72) Inventors: Rizwan Hassan, Danville, CA (US); Juergen Schultheiss, Cologne (DE); Lorenzo Miguelino Marte, Los Gatos, CA (US); Jean-Paul Etienne Sier, San jos, CA (US); Michael Poier, Overath (DE)

(73) Assignees: Varian Medical Systems Particle Therapy GMBH, Troisdorf (DE); Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 16/794,829

(22) Filed: Feb. 19, 2020

(65) Prior Publication Data
US 2020/0179724 A1    Jun. 11, 2020

Related U.S. Application Data

(63) Continuation of application No. 15/458,780, filed on Mar. 14, 2017, now Pat. No. 10,603,518.

(51) Int. Cl.
*A61N 5/00* (2006.01)
*A61N 5/10* (2006.01)
(Continued)

(52) U.S. Cl.
CPC .......... *A61N 5/1081* (2013.01); *A61N 5/1043* (2013.01); *A61N 5/1049* (2013.01);
(Continued)

(58) Field of Classification Search
CPC .. A61N 5/1081; A61N 5/1043; A61N 5/1049; A61N 2005/1061; A61N 2005/1087
(Continued)

(56) References Cited

U.S. PATENT DOCUMENTS

| 4,507,616 A | * | 3/1985 | Blosser | ..................... | A61N 5/10 |
| | | | | | 250/492.3 |
| 4,641,104 A | * | 2/1987 | Blosser | ..................... | H05H 7/20 |
| | | | | | 250/493.1 |

(Continued)

FOREIGN PATENT DOCUMENTS

| EP | 2308561 A1 | 4/2011 |
| JP | S5645174 U | 4/1981 |

(Continued)

*Primary Examiner* — Michael Maskell (57) ABSTRACT

A proton beam therapy system with a cantilever gantry. The cantilever gantry has one end portion (the fixed end portion) affixed to an external structure that supports the weight of the gantry. The remainder of the gantry is suspended and the free end portion is coupled to a beam nozzle. A main bearing is coupled to the fixed end portion and enables the gantry to rotate in a full range of 360° around the iso-center. A large counterweight can be disposed in the fixed end portion to keep the system center of mass close to the bearing. The gantry may have a monocoque housing, including a cantilever section enclosing the magnets and other components of the gantry beamline and a drum section on which the bearing is placed.

17 Claims, 8 Drawing Sheets

(51) Int. Cl.
*H05H 7/04* (2006.01)
*H05H 7/00* (2006.01)

(52) U.S. Cl.
CPC ............... *A61N 2005/1061* (2013.01); *A61N 2005/1087* (2013.01); *H05H 2007/002* (2013.01); *H05H 2007/048* (2013.01)

(58) Field of Classification Search
USPC .......................................... 250/492.1–492.3
See application file for complete search history.

(56) References Cited

U.S. PATENT DOCUMENTS

| | | | | |
|---|---|---|---|---|
| 8,536,547 | B2* | 9/2013 | Maurer, Jr. | A61N 5/1081 |
| | | | | 250/492.3 |
| 8,629,415 | B2* | 1/2014 | Fadler | A61B 6/0407 |
| | | | | 250/491.1 |
| 8,748,852 | B2* | 6/2014 | Jongen | A61N 5/10 |
| | | | | 250/492.3 |
| 8,975,602 | B2 | 3/2015 | Huber et al. | |
| 10,603,518 | B2 | 3/2020 | Hassan et al. | |
| 2005/0161618 | A1* | 7/2005 | Pedroni | A61N 5/1081 |
| | | | | 250/492.3 |
| 2007/0018117 | A1* | 1/2007 | Calderon | A61N 5/1048 |
| | | | | 250/492.1 |
| 2007/0284548 | A1* | 12/2007 | Kaiser | A61N 5/01 |
| | | | | 250/522.1 |
| 2008/0179544 | A1* | 7/2008 | Kaiser | A61N 5/10 |
| | | | | 250/492.1 |
| 2009/0200483 | A1* | 8/2009 | Gall | A61N 5/1081 |
| | | | | 250/396 R |
| 2011/0266464 | A1* | 11/2011 | Takai | G06Q 50/22 |
| | | | | 703/2 |
| 2012/0168646 | A1* | 7/2012 | Gutfleisch | A61N 5/10 |
| | | | | 250/492.1 |
| 2012/0280150 | A1* | 11/2012 | Jongen | A61N 5/10 |
| | | | | 250/492.3 |
| 2015/0087884 | A1* | 3/2015 | Huber | A61N 5/1081 |
| | | | | 600/1 |
| 2016/0279447 | A1* | 9/2016 | Timmer | A61N 5/1081 |
| 2017/0028224 | A1* | 2/2017 | Gall | H05H 13/04 |
| 2018/0028835 | A1 | 2/2018 | Bennett | |

FOREIGN PATENT DOCUMENTS

| | | |
|---|---|---|
| JP | S5675174 A | 6/1981 |
| JP | S5645174 B2 * | 10/1981 |
| JP | S62183775 A | 8/1987 |
| JP | 2011250910 A | 12/2011 |
| WO | 2011053960 A1 | 5/2011 |
| WO | 2013093020 A1 | 6/2013 |
| WO | 2014041003 A2 | 3/2014 |
| WO | 2015042535 A1 | 3/2015 |

\* cited by examiner

FIG. 8

ROTATABLE CANTILEVER GANTRY IN RADIOTHERAPY SYSTEM

RELATED APPLICATIONS

This application is a continuation of, and claims the benefit of and priority to, application Ser. No. 15/458,780 Entitled "Rotatable Cantilever Gantry In Radiotherapy System" filed on Mar. 14, 2017 which is incorporated herein by reference.

TECHNICAL FIELD

The present disclosure relates generally to the field of radiation therapy systems, and, more specifically, to gantries in radiation therapy systems.

BACKGROUND OF THE INVENTION

In a typical proton therapy system used for tumor radiation treatment for example, a proton beam is generated and output from an accelerator, e.g., a cyclotron or a synchrotron, with a certain initial energy. The initial energy determines a maximum penetration depth of the proton beam and typically is 250 MeV. As the proton beam travels through a beam transportation system or a beamline, the beam energy is precisely tuned through energy selection mechanisms, e.g., an energy degrader or energy slit. The beam transport system includes a plurality of magnets for beam redirection (bending), focusing and steering. A rotational gantry with a radiation nozzle is located at the end of the beam transport system. Eventually, the beam is delivered to a treatment station and irradiated onto a patient at an energy level prescribed for the specific treatment session based on the tumor volume, geometry, location and etc.

Due to the extremely high cost for purchasing and maintaining such a radiation system, a medical facility usually uses one accelerator for a plurality of treatment stations so the high expenditure for the accelerator facilities is distributed. Although using a multi-station single-cyclotron system is effective to distribute the cost for large medical facilities, the overall cost for such a multi-gantry system can be prohibitively high for smaller healthcare facilities that may only need one treatment station. Also, some multi-station systems do not support simultaneous treatment in multiple stations. This contribute to further disadvantage that a delay at one treatment station can cause delay at the other station.

With the demand for proton beam radiation therapy rising worldwide, smaller and less expensive proton therapy systems are highly desired to increase patient access to therapy. In a proton radiation system, a gantry system alone typically weighs over 200 tons which is mainly contributed by the massive magnets installed in the gantry. To support and precisely control the motion of a tremendous amount of weight, existing rotatable gantries are supported by a front and a rear ring structures, between which the components in the gantry beamline are suspended. That is, the gantry is supported in a simply-supported manner.

Figure 1:
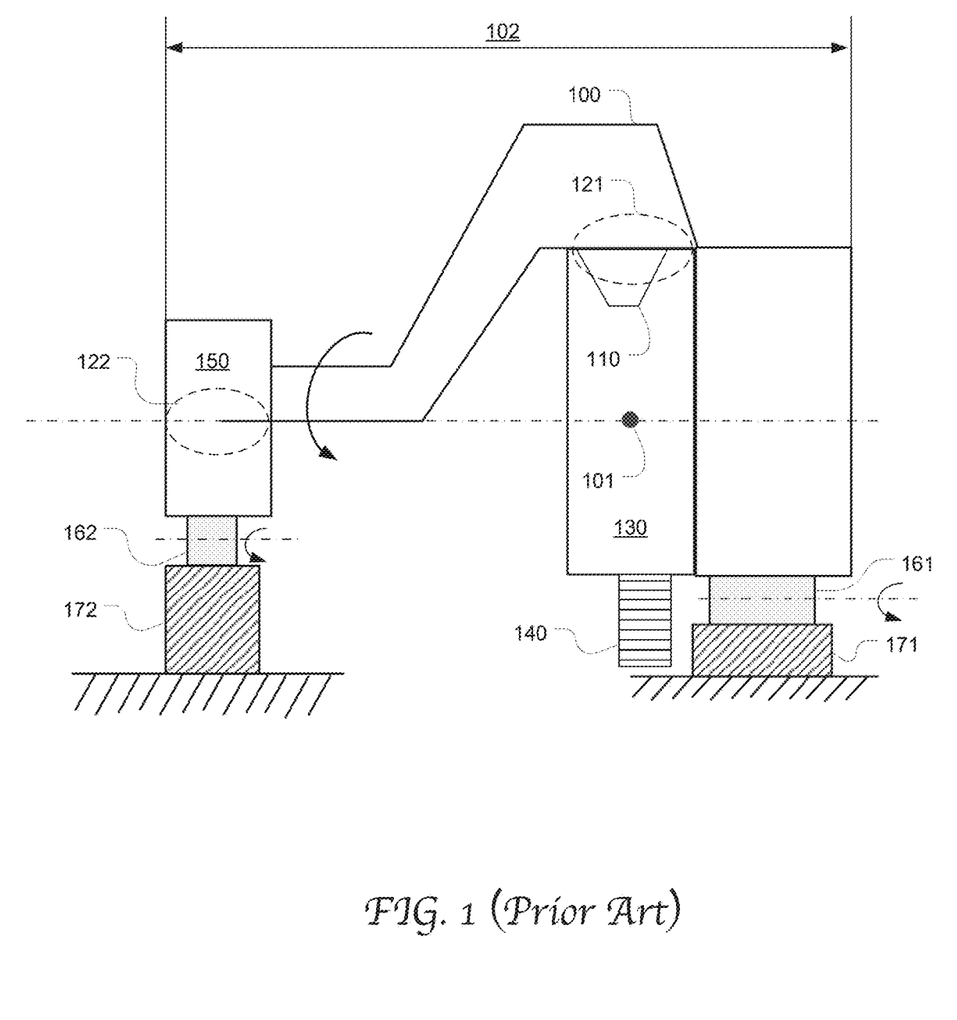
FIG. 1 illustrates the supporting mechanism of a simply-supported gantry in a proton beam therapy system according to the prior art.

FIG. 1 illustrates the supporting mechanism of a simply-supported gantry 100 in a proton beam therapy system according to the prior art. The gantry 100 includes beam optics (or a beamline) coupled to a beam nozzle 110. A series of magnets (not shown) in the beamline operate to guide the transportation of a proton beam which eventually exits from the beam nozzle 110 and is irradiated onto a patient. The gantry 100 rotates around the iso-center 101 which defines the positioning of a treatment table and a patient during operation.

Supported in a simply-supported manner, the weight of the gantry 100 is supported at both end portions of the gantry (as illustrated by the dotted circles 121 and 122). More specifically, a front ring 120 and a rear ring 150 are respectively coupled to the front and rear ends of the gantry 100. The front and rear rings 120 and 150 are respectively coupled to the front and rear rollers 161 and 162 that can rotate with the gantry 100. The rings and rollers are affixed to the ground through fixtures 171 and 172 which are made of steel and concrete.

The two rings 130 and 150, plus the additional structural members to stiffen the assembly, make the gantry system appear to be a tremendously large conical (generally tapering from right to left as illustrated) or cylindrical drum-shaped structure in a treatment station. The drum-shaped structure defines the overall size of the gantry, such as the end-to-end gantry length 102. Such a drum-shaped gantry undesirably limits patient positioning and makes it difficult to make incremental improvements to the beam optics geometry because the critical dimensions are determined by the mechanical structure, not by the magnet positioning.

More importantly, using two rollers to support introduces random deflection errors during rotation due to the inherent difficulty in aligning the two rollers perfectly. As a result, the gantry tends to wobble causing the beam spot location to shift in an unpredictable manner. In practice, remarkable time and resources are usually spent on realigning and repositioning the rollers in the attempt to fix the random errors and maintain beam precision.

SUMMARY OF THE INVENTION

Accordingly, disclosed herein provide a rotatable gantry assembly for a proton therapy system having a structure support mechanism that allows a compact and lightweight design of the gantry and yet offers improved mechanical reliability and beam precision.

Embodiments of the present disclosure include a gantry that is configured as an open-ended cantilever arm with one end portion (the fixed end portion) affixed to an external structure that supports the weight of the gantry. The remainder of the gantry is cantilevered and the free end portion and coupled to a beam nozzle. A main bearing is coupled to the fixed end portion and enables the gantry to rotate in a full range of 360° around the iso-center. A large counterweight can be disposed in the fixed end portion to keep the system center of mass close to the bearing. The housing of the gantry may be composed of one or more monocoque sections, for example, a cantilever section enclosing the magnets and other components of the gantry beamline and a drum section on which the bearing is placed.

According to embodiments of the present disclosure, the weight of a proton beam gantry is supported in a cantilevered manner at one location, e.g., through a main bearing. Compared with the simply-supported gantries in the conventional proton beam therapy systems, a cantilever gantry advantageously eliminates the need for a roller or a bearing or other support structure around the treatment area and thereby removes a major source of random deflection errors. The cantilevered design is de-coupled from the gantry rotating mechanism, advantageously allowing the beam geometry to be modified without significantly changing the rotating bearing structure. Further, with the simplified supporting mechanism, a cantilever gantry can be made compact and lightweight, allowing significantly improved flexibility in the positioning of a patient while maintaining the full range rotation capacity of the gantry. Moreover, by using monocoque housing, a gantry according to the present disclosures can be delivered to a healthcare facility as a fully-assembly, pre-tested unit. Consequently, the expenditure associated with manufacture, transportation, installation, assembling and maintenance can be dramatically and advantageously decreased.

BRIEF DESCRIPTION OF THE DRAWINGS

Embodiments of the present invention will be better understood from a reading of the following detailed description, taken in conjunction with the accompanying drawing figures in which like reference characters designate like elements and in which.

DETAILED DESCRIPTION

Reference will now be made in detail to the preferred embodiments of the present invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail so as not to unnecessarily obscure aspects of the embodiments of the present invention.

Although a method may be depicted as a sequence of numbered steps for clarity, the numbering does not necessarily dictate the order of the steps. It should be understood that some of the steps may be skipped, performed in parallel, or performed without the requirement of maintaining a strict order of sequence. The drawings showing embodiments of the invention are semi-diagrammatic and not to scale and, particularly, some of the dimensions are for the clarity of presentation and are shown exaggerated in the drawing Figures. Similarly, although the views in the drawings for the ease of description generally show similar orientations, this depiction in the Figures is arbitrary for the most part. Generally, the invention can be operated in any orientation.

Rotatable Cantilever Gantry in Radiotherapy System

Overall, embodiments of the present disclosure provide a radiotherapy system including a rotatable gantry with its weight supported in a cantilevered manner. The fixed end portion of the cantilever gantry has a main bearing enabling the gantry to rotate in 360° around an iso-center. The open end portion of the cantilevered gantry is suspended and coupled to a beam nozzle used to irradiate a particle beam onto a patient positioned according to the iso-center.

Figure 2:
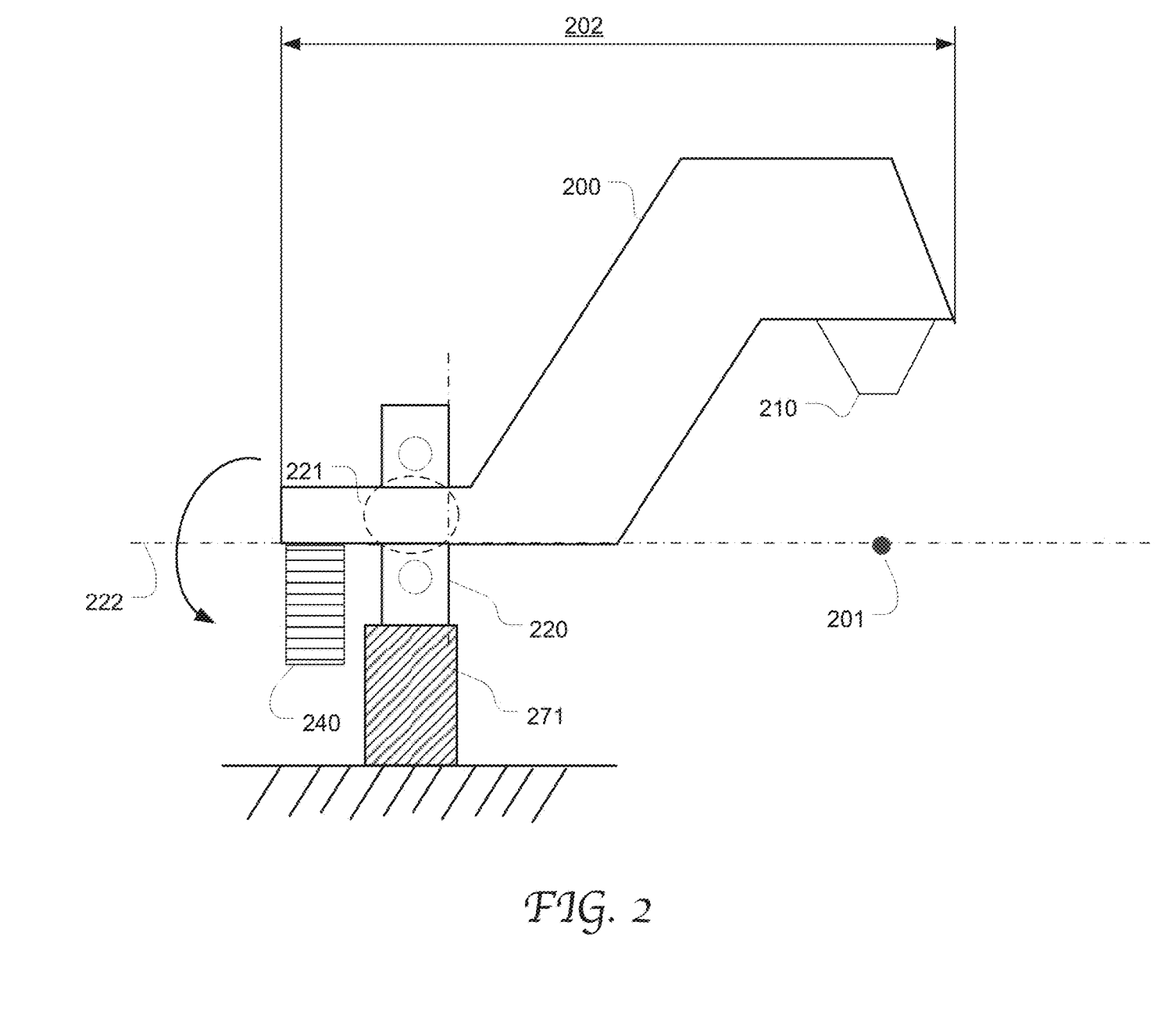
FIG. 2 illustrates the supporting mechanism of an exemplary cantilever gantry in a proton beam therapy system according to an embodiment of the present disclosure.

FIG. 2 illustrates the supporting mechanism of an exemplary cantilever gantry 200 that can be used in a proton beam therapy system according to an embodiment of the present disclosure. The cantilever gantry 200 includes a gantry beamline (not shown) for transporting a proton beam to the beam nozzle 210. A series of magnets in the gantry beamline operate to direct the beam transportation. The proton beam is eventually irradiated onto a patient through the beam nozzle. The cantilever gantry 200 can rotate around the iso-center 201 which defines the positioning of a treatment table (not shown) and so a patient during operation.

In some embodiments, the gantry beamline 200 is equipped with a pencil beam scanning nozzle using scanning magnets to control the lateral positions (X and Y) of the beam spot according to a predetermined scanning position (e.g., in spot scanning) or scanning path (e.g., in raster scanning). The gantry beamline also includes the first and the second (final) dipole magnets as the bending magnets, the quadrupole magnets as focusing magnets, and steering and correction magnets for centering the beam in the beamline. Typically, the two dipole magnets bend the proton beam by 90° in total. More specifically, the first dipole magnet is operable to bend the proton beam by an acute angle, e.g., 50°, and the second dipole magnet is operable to bend the proton beam by an obtuse angle, e.g., 140°.

According to the present disclosure, the cantilever gantry 200 is configured as a cantilevered arm having a fixed end portion mounted to an external supporting structure 271 and an open end portion coupled to the beam nozzle 210. More specifically, the weight of the cantilever gantry 200 is supported at one location as indicated by the dotted circle 221. The remainder of the gantry is suspended. The free end portion is coupled to the beam nozzle 210. Thus, compared with a conventional simply-supported gantry as illustrated in FIG. 1, a cantilever gantry according to the present disclosure eliminates the need for a bearing or a roller or other support structure around the treatment area. Thereby random deflection errors caused by misalignment between two supporting rollers are removed. Also, the end-to-end gantry length 202 of a cantilever gantry can be much shorter.

A large counterweight 240 can be disposed in the fixed end portion to keep the system center of mass close to the supporting area (as indicated by the dotted circle 221) of the gantry 200.

In some embodiments, the external supporting structure 271 is mounted on the ground or a building wall. However, the present disclosure is not limited by the configuration of the external support structure. Nor is it limited by the affixation technique or mechanism used to couple the gantry to an external support structure.

A main bearing 220 is installed in the fixed end portion 220 such that the cantilever gantry 200 can rotate about the axis 222, e.g., in a full range of 360°. The gantry beamline runs through the interior of the bearing. In this example, the main bearing is coupled to the external supporting structure 271 and also serves to support the weight of the cantilever gantry. However, it will be appreciated that a cantilever gantry can be supported in a range of other suitable locations along the gantry without departing from the scope of the present disclosure.

In some example the main bearing is disposed around the first bending magnet or adjacent to one end of it. The main bearing may be a slew bearing sufficiently large to encompass the sweeping volume of the first bending magnet. However, the main bearing may also be implemented in any other suitable technology and configuration without departing from the scope of the present disclosure. Further, in some other embodiments, a rotating mechanical component other than a bearing can be used to enable rotational motion of the cantilever gantry.

Therefore, according to embodiments of the present disclosure, a proton beam gantry is configured as a cantilever arm and its weight is supported in a cantilevered manner from one location, e.g., through the main bearing. The cantilevered gantry design is de-coupled from the rotating mechanism, advantageously allowing the beam optics geometry to be modified without significantly changing the rotating bearing structure. Further, with the simplified supporting mechanism, a cantilever gantry can be made compact and lightweight, allowing significant flexibility in the positioning of a patient while maintaining the full range rotation capacity.

In some embodiments, a cantilever gantry can be configured and manufactured as a separate system from the beam delivery system (e.g., a beam nozzle) and imaging systems (e.g., used in a positioning verification system). The cantilever gantry is equipped with interface structures with the external beam delivery system and the imaging systems. In this manner, the beam optics can be changed without changing the rotating mechanical structure. However, in some other embodiments, a beam delivery system and imaging systems are integral parts of a cantilever gantry.

Most current 360° gantries are assembled on-site, requiring the beamline to be fitted and aligned while the gantry is constructed. A significant number of cables and equipments are fitted on-site, leading to variations in installation quality and duration as well as very high installation cost. According to the present disclosure, a cantilever gantry may be manufactured and delivered to a health care facility as a fully-assembled, pre-tested unit, with the beamline factory-assembled and aligned, as well as the beam nozzle, all the cables, vacuum and plumbing systems, motor brakes, rotation drive mechanisms, media chains, imaging devices, and etc. It will be appreciated that a cantilever gantry according to the present disclosure may include a wide range of components that are well known in the art, such as energy selection system (ESS) with an energy degrader, an in-situ beam diagnostic mechanism used to monitor beam position and beam current, and etc.

Figure 3:
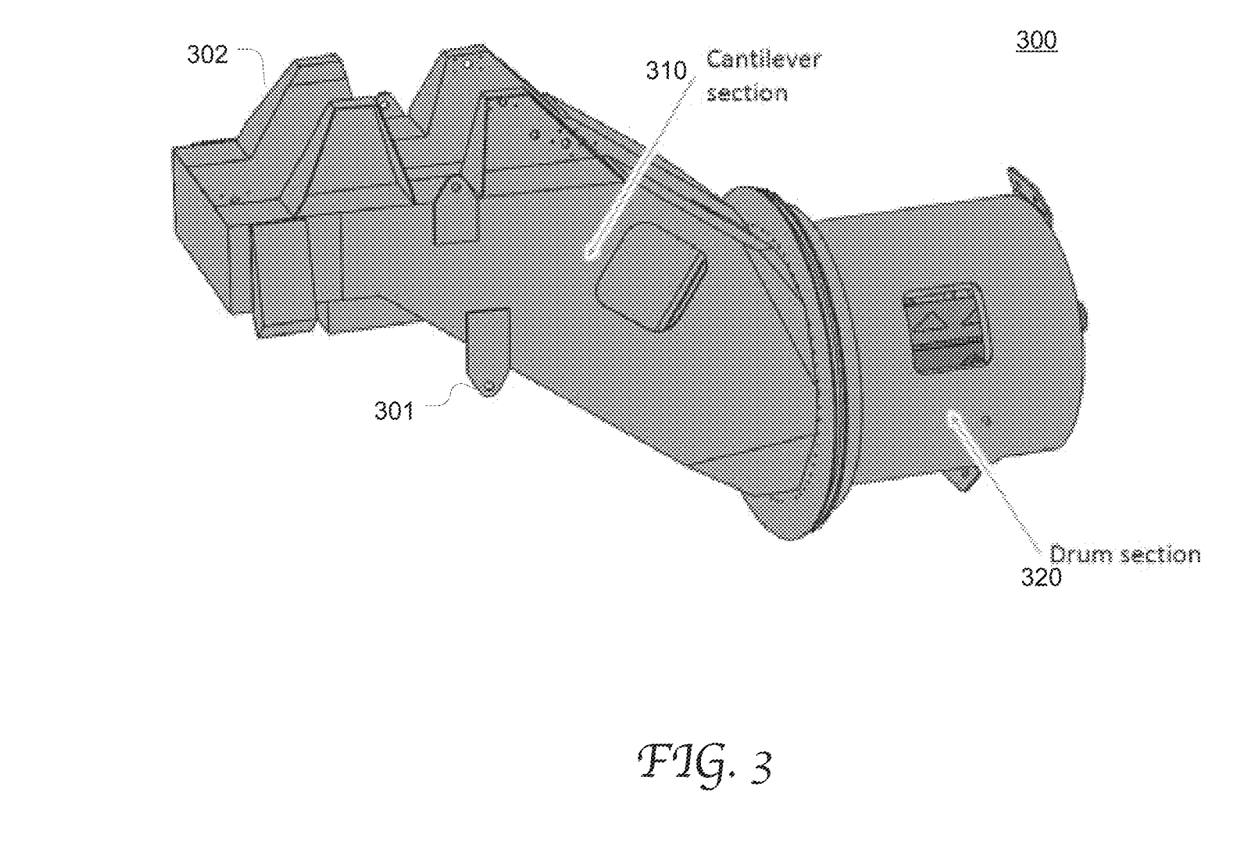
FIG. 3 illustrates an exemplary monocoque housing in a cantilever gantry according to an embodiment of the present disclosure.

In some embodiments, a cantilever gantry includes a monocoque or fully integrated box structure used as the frame or exterior housing. The present disclosure is not limited by the material compositions, configuration or geometry of monocoque housing of a cantilever gantry. FIG. 3 illustrates an exemplary monocoque housing 300 in a cantilever gantry according to an embodiment of the present disclosure.

The monocoque housing 300 may be fully welded and includes a cantilever section 310 and a drum section 320. Alternatively, the two sections may be separate monocoque parts and coupled together through another coupling mechanism. The main bearing may be disposed at the joint area of the two sections. Each section of the monocoque housing may be a fully welded steel monocoque or box structure. The cantilever section 310 may contain the gantry beamline starting after the first bending magnets and the associated components. A nozzle may be coupled to, or enclosed in, the open end of the cantilever section 310 that extends over the treatment room. An imaging system may also be mounted to the cantilever section 310. The drum section 320 is substantially cylindrical and may enclose, or otherwise is coupled with, the main bearing, the signal and power cables, the beamline up to the first bending magnet, vacuum and plumbing components, emergency motor brakes, rotation drive mechanisms, the counterweight, media chains and/or imaging devices. The monocoque housing 300 includes protrusions or other features formed to fit the various components of the gantry.

The cantilever section 310 may be constructed of welded steel plates which form the load-carrying outer skin. The cantilever section 310 may be made increasingly stiffer toward the main bearing location to counter the significant forces imposed in this region. In some embodiments, the base (fixed end portion) of the cantilever gantry is stiffened by increasing the plate thickness near the main bearing. The drum section 320 can be constructed from a heavy wall steel tube.

Monocoque housing in a gantry advantageously provides superior stiffness-weight ratio, particularly for torsional load created by the heavy second bending dipole when the gantry rotates to the ±90° positions. The cantilever section 310 may have a generally tapered shape in various directions, with its open end much narrower than the joint end. This can help maintain stiffness of the gantry through all angles of rotation.

Moreover, by using monocoque housing, a gantry according to the present disclosures can be delivered to a health care facility as a fully-assembly, pre-tested unit. Consequently, the expenditure associated with manufacturing, transportation, installation, assembling and maintenance can be dramatically and advantageously decreased.

Figure 4:
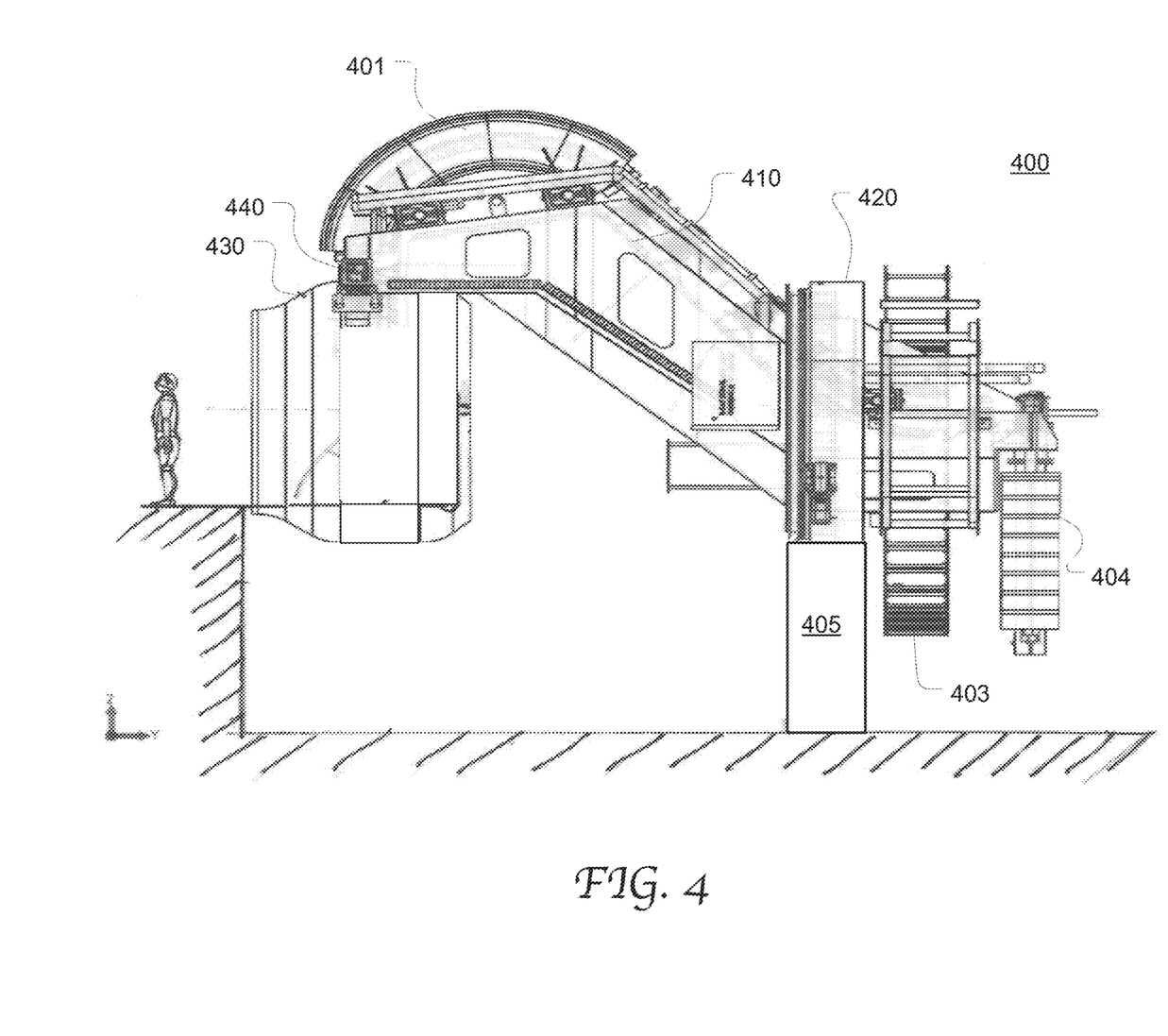
FIG. 4 illustrates the interior configuration of an exemplary cantilever gantry installed in a treatment room according to an embodiment of the present disclosure.

FIG. 4 illustrates the interior configuration of an exemplary cantilever gantry 400 installed in a treatment room according to an embodiment of the present disclosure. The cantilever gantry 400 includes a monocoque housing 410 (partially shown), a final bending magnet 401 in its open end portion and a main bearing in its fixed end portion. The cantilever gantry 400 is affixed to an external support structure 405 through the main bearing 402. The open end of the gantry is coupled to a beam nozzle 440 and gantry cover 430, both capable of rotating with the gantry 400. The gantry cover 430 is useful to block users' view into the gantry structure. An energy chain 403 (or cable chain) and a counterweight 404 are mounted on the fixed end portion of the gantry 400.

Figure 5:
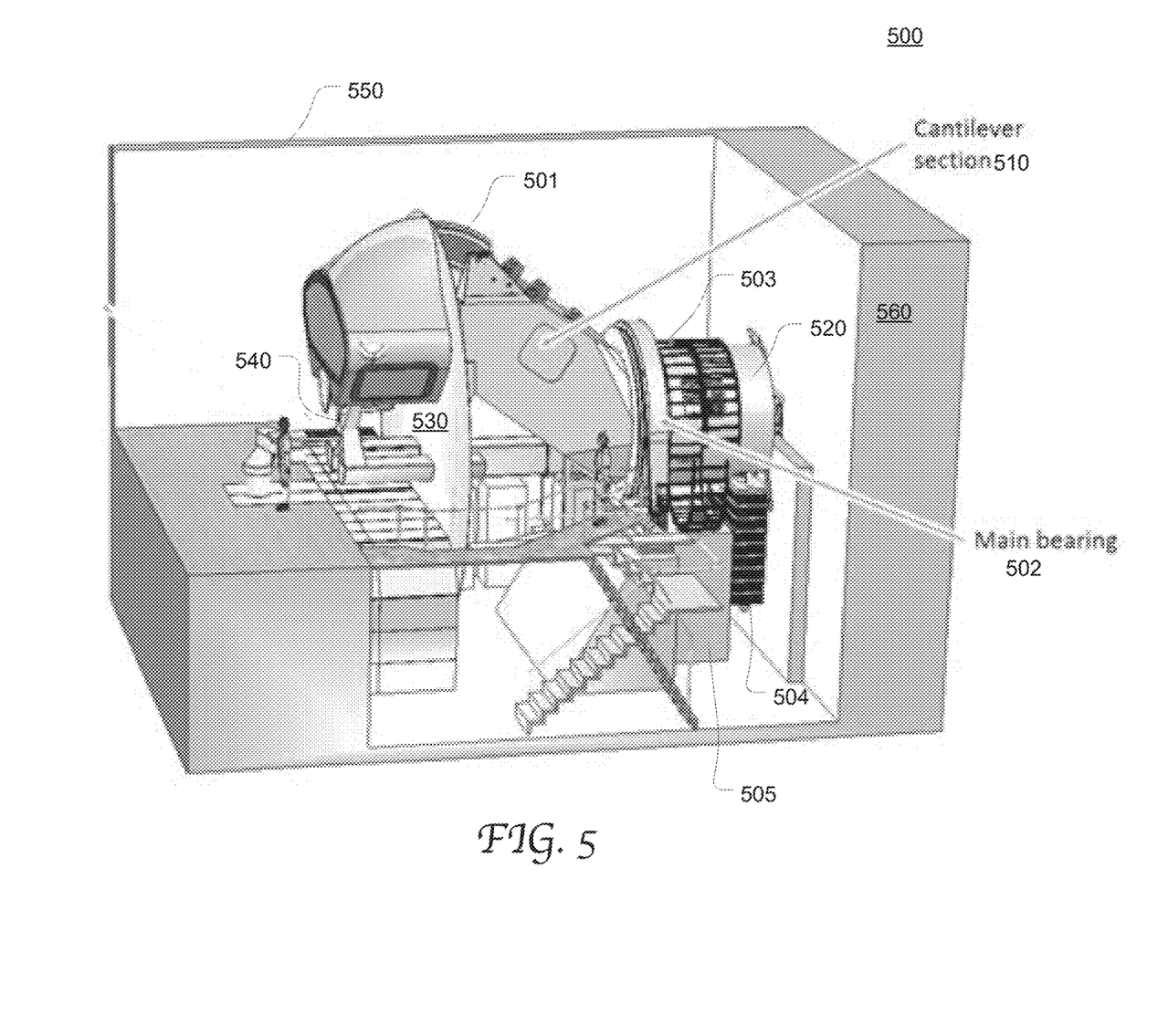
FIG. 5 illustrates the configuration of an exemplary cantilever gantry installed in a treatment room according to an embodiment of the present disclosure.

FIG. 5 illustrates the configuration of an exemplary cantilever gantry 500 installed in a treatment room 550 according to an embodiment of the present disclosure. The cantilever gantry 500 has a similar configuration as the cantilever gantry 400 in FIG. 4. The cantilever gantry 500 includes a final bending magnet 501 in its open end portion, a main bearing 502 located in its fixed end portion, and a monocoque housing (partially shown). The main bearing 502 is coupled between the cantilever section 510 and the drum section 520 of the monocoque housing. The weight of the cantilever gantry 500 is supported by an external supporting structure 505 rising from the ground. The end of the drum section 520 is affixed to an external wall 560 of the treatment room 550. A counterweight 504 is attached to the drum section 520 near the external wall 560. The open end of the cantilever gantry 500 has a beam nozzle 540 pointing to the iso-center. A gantry cover 530 is coupled to the end portion of the cantilever gantry 500.

Figure 6:
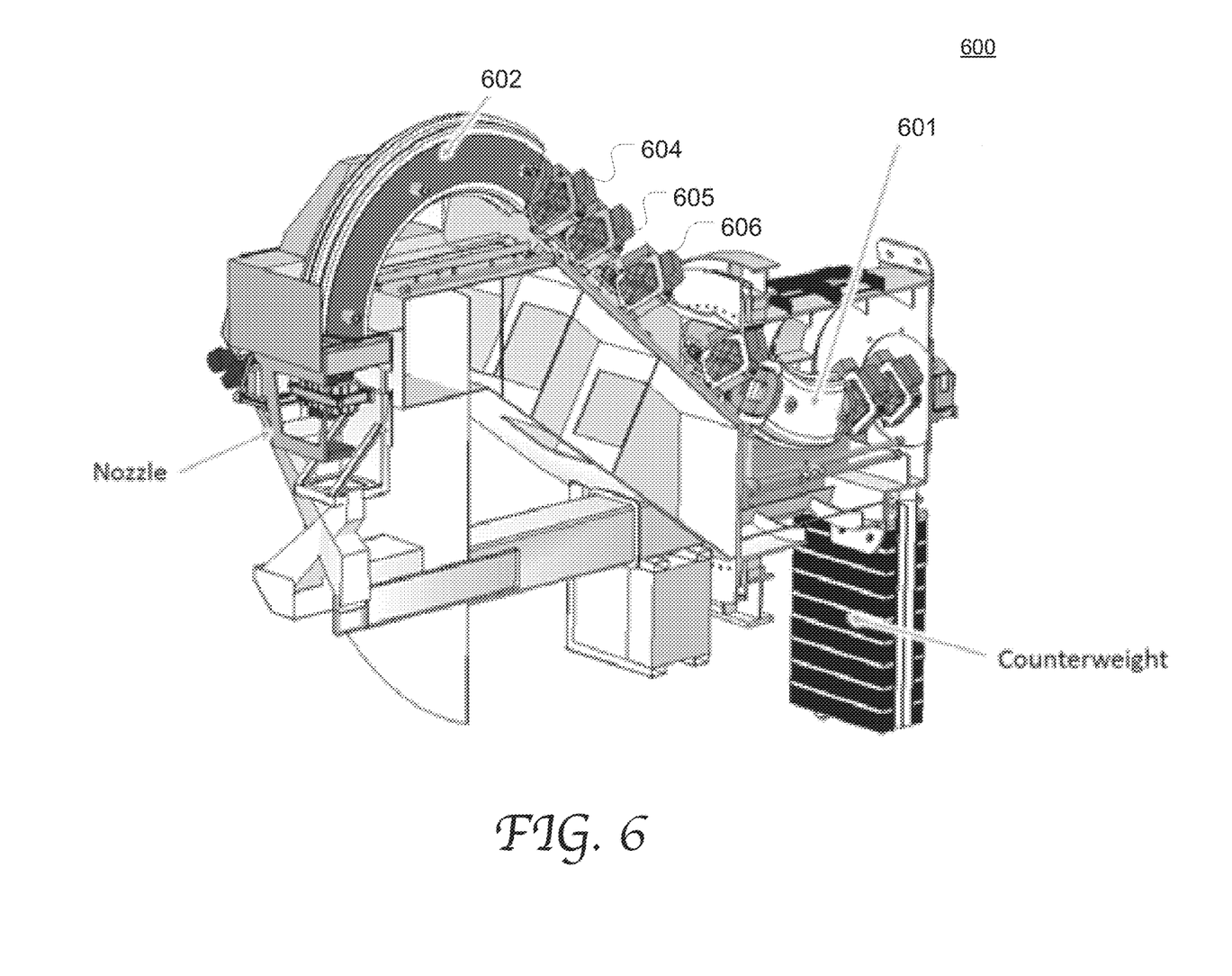
FIG. 6 illustrates the configuration of the interior components in an exemplary cantilever gantry according to an embodiment of the present disclosure.

FIG. 6 illustrates the configuration of the interior components in an exemplary cantilever gantry 600 according to an embodiment of the present disclosure. The cantilever gantry 600 has a similar configuration as the cantilever gantry 500 in FIG. 5. The gantry beamline includes the first dipole magnet 601 and the second dipole magnet 602, and quadrupole magnets 604-606 serving as focusing magnets. In this example, the first dipole magnet 601 is operable to bend the proton beam by 50°, and the second dipole magnet 602 is operable to bend the proton beam by 140°.

Figure 7:
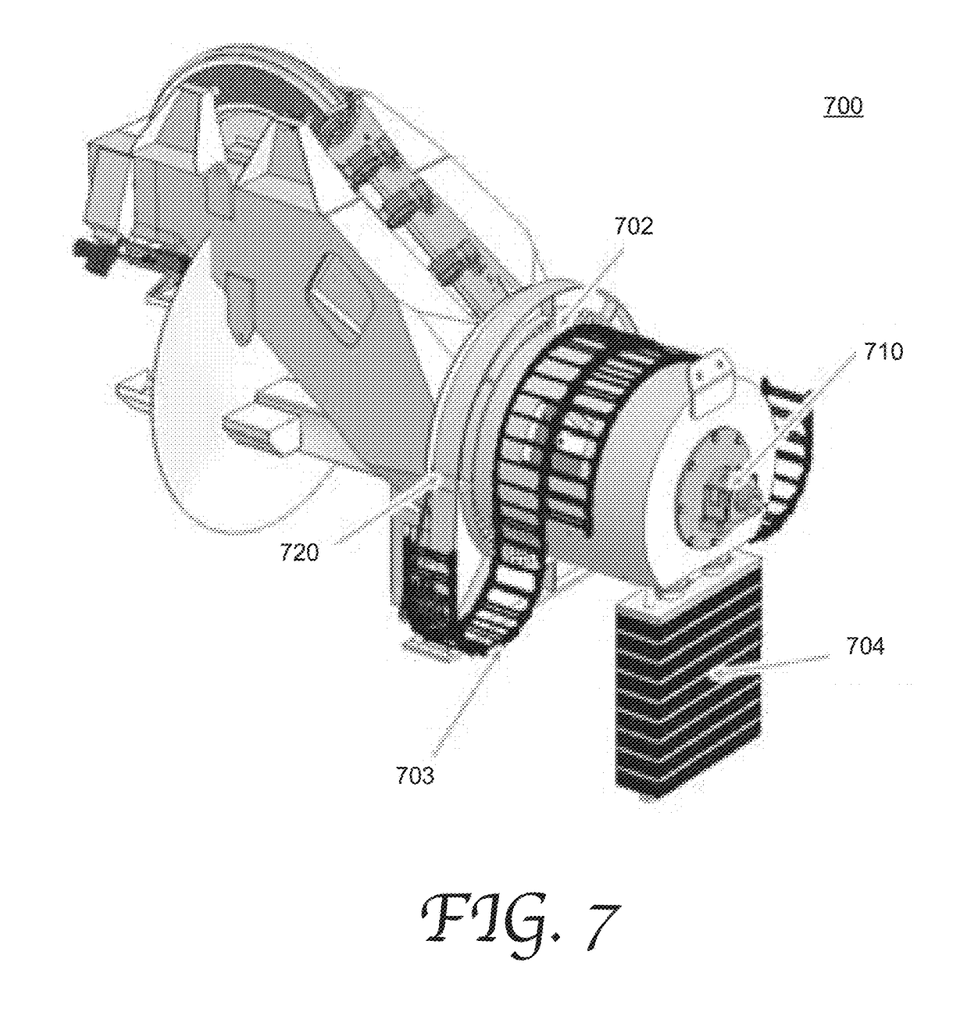
FIG. 7 illustrates the configuration of an exemplary cantilever gantry according to an embodiment of the present disclosure.

FIG. 7 illustrates the configuration of an exemplary cantilever gantry 700 according to an embodiment of the present disclosure. The cantilever gantry 700 has a similar configuration as the cantilever gantry 600 in FIG. 6. The main bearing 702 is covered by a main bearing housing 720 which may or may not be an integral part of the monocoque housing of the cantilever gantry 700. A media chain 703 is disposed on the drum section of the housing and integrates the flexible wires, cables and others.

In this example, besides the main bearing 702, a rear bearing 710 is optionally installed at the other end of the drum section. The rear bearing 710 may be much smaller than the main bearing as it needs not encompass the sweep of the large bending magnet. Depending on the exact center of mass of the gantry and the moment-carrying capacity of the main bearing and main bearing housing, the rear bearing 710 may be omitted in some embodiments.

Figure 8:
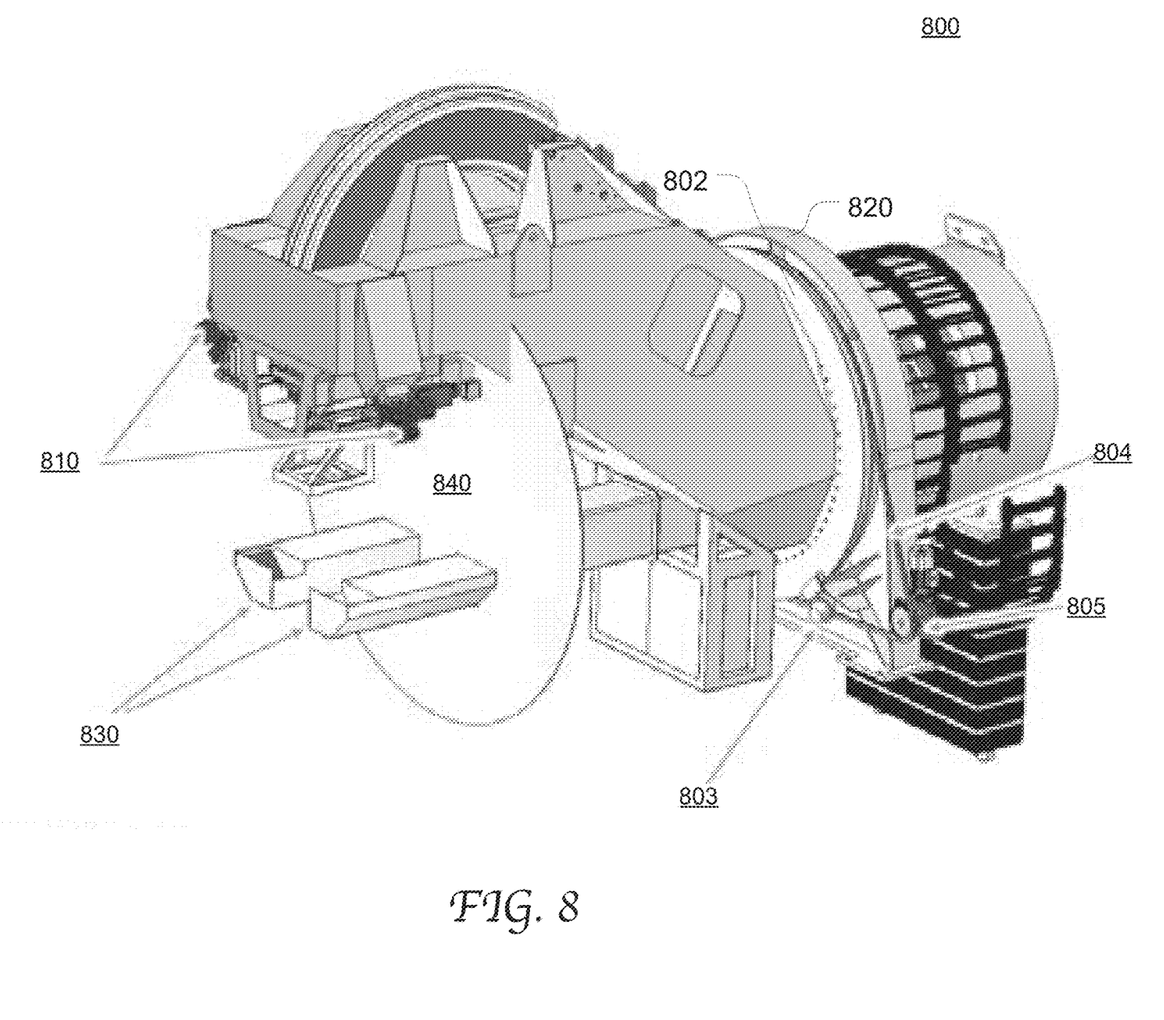
FIG. 8 illustrates the configuration of an exemplary cantilever gantry according to an embodiment of the present disclosure.

FIG. 8 illustrates the configuration of an exemplary cantilever gantry 800 according to an embodiment of the present disclosure. The cantilever gantry 800 has a similar configuration as the cantilever gantry 600 in FIG. 6. The main bearing 802 is covered by a main bearing housing 820. In addition, a rotation drive chain 804, a rotation drive motor 805 and an emergency motor brake 803 are coupled to the main bearing 802. These units can be implemented in any manner that is well known in the art. The open end of the cantilever gantry 800 is coupled with positioning verification system (PVS) X-ray tubes 810 and a gantry cover 840. The retractable PVS imaging panels 830 extend from the gantry cover 840.

Although certain preferred embodiments and methods have been disclosed herein, it will be apparent from the foregoing disclosure to those skilled in the art that variations and modifications of such embodiments and methods may be made without departing from the spirit and scope of the invention. It is intended that the invention shall be limited only to the extent required by the appended claims and the rules and principles of applicable law.

What is claimed is:

1. A radiotherapy system comprising:
   a beam nozzle;
   a gantry assembly comprising a gantry beamline configured to transport the particle beam to the beam nozzle, wherein the gantry assembly is configured to rotate around an iso-center of the radiotherapy system;
   a support member operable to be coupled to an external surface, the support member configured to support the gantry assembly in a cantilevered manner, wherein the support member includes a main bearing and the gantry beamline runs through the interior of the main bearing; and
   a counterweight coupled to the gantry assembly, wherein the counterweight is proximate a first side of the main bearing and the nozzle is proximate a second side of the main bearing, wherein the first side and second side are opposite sides of the main bearing, and wherein the beamline passes by the counter weight and through the main bearing before an initial beamline bend in the gantry assembly.

2. The radiotherapy system of claim 1, wherein the main bearing is configured to enable the gantry assembly to rotate around the iso-center in a range of 360°.

3. The radiotherapy system of claim 1 wherein a monocoque housing is configured to enclose the gantry beamline.

4. The radiotherapy system of claim 3 wherein an imaging system and a cable chain are coupled to the gantry assembly through the monocoque housing.

5. The radiotherapy system of claim 3, wherein the monocoque housing comprises:
   a cantilever arm section that tapers toward the free end of the gantry assembly; and
   a drum section in a cylinder-like shape and operable to be coupled to the counterweight.

6. The radiotherapy system of claim 5, wherein the drum section of the monocoque housing is further configured to enclose one or more of: the main bearing, a rotation drive system, a positional feedback system, and an emergency motor brake.

7. The radiotherapy system of claim 5, wherein the support member is operable to be affixed to an external wall.

8. The radiotherapy system of claim 1, wherein a first dipole magnet is disposed proximate to the free end of the gantry assembly and the second dipole magnet is disposed proximate to the fixed end of the gantry assembly.

9. The radiotherapy system of claim 4, wherein the support member is disposed proximate to the first dipole magnet.

10. A proton beam therapy system comprising:
    a beam nozzle;
    a gantry assembly comprising a gantry beamline configured to transport the particle beam to the beam nozzle, wherein the gantry assembly is configured in a monocoque housing and rotates around an iso-center of the radiotherapy system;
    a support member operable to be coupled to an external surface, the support member configured to support the gantry assembly in a cantilevered manner, wherein the support member includes a main bearing and the gantry beamline runs through the interior of the main bearing; and
    a cable chain coupled to the gantry assembly through the monocoque housing.

11. The proton beam therapy system of claim 10, wherein the monocoque housing is configured to contain and support the gantry beamline and the bearing.

12. The proton beam therapy system of claim 11, wherein the gantry assembly comprises a bearing configured to enable the gantry assembly to rotate around the iso-center in a range of 360°.

13. The proton beam therapy system of claim 10, wherein the monocoque housing is further configured to contain and support the bearing.

14. The proton beam therapy system of claim 10, wherein the monocoque housing comprises:
- a cantilever arm section that tapers toward the free end of the gantry assembly; and
- a drum section in a cylinder-like shape and coupled to the counterweight.

15. The proton beam therapy system of claim 14, wherein the drum section is further configured to enclose one or more of: the bearing; a rotation drive system; a positional feedback system; an emergency motor brake.

16. The proton beam therapy system of claim 10 further comprising a counterweight coupled to the gantry assembly, wherein the counterweight is proximate a first side of the main bearing and the nozzle is proximate a second side of the main bearing, wherein the first side and second side are opposite sides of the main bearing, and wherein the beamline passes by the counter weight and through the main bearing before an initial bend in the gantry assembly.

17. The proton beam therapy system of claim 13, wherein the monocoque housing is a fully welded monocoque structure.

* * * * *